United States Patent [19]
Hirschman et al.

[11] Patent Number: 5,940,161
[45] Date of Patent: *Aug. 17, 1999

[54] METHOD AND KIT FOR ATTACHING SIDE SHIELDS TO EYEGLASS TEMPLES

[75] Inventors: Richard Hirschman, Bohemia, N.Y.; Wayne Jerman, Dallas, Tex.

[73] Assignee: Hudson Optical Corporation, Bohemia, N.Y.

[*] Notice: This patent is subject to a terminal disclaimer.

[21] Appl. No.: 09/092,436

[22] Filed: Jun. 5, 1998

Related U.S. Application Data

[63] Continuation of application No. 08/656,640, May 31, 1996, Pat. No. 5,798,815.

[51] Int. Cl.⁶ .............................. G02C 7/10; G02C 13/00
[52] U.S. Cl. ........................... 351/44; 351/121; 351/178; 2/13; 2/449
[58] Field of Search .............................. 351/44, 111, 116, 351/121, 158, 178, 47; 2/13, 448, 449, 450, 451

[56] References Cited

U.S. PATENT DOCUMENTS

| | | | |
|---|---|---|---|
| 5,543,864 | 8/1996 | Hirschman et al. | 351/44 |
| 5,798,815 | 8/1998 | Hirschman et al. | 351/44 |

Primary Examiner—Huy Mai
Attorney, Agent, or Firm—Ostrolenk, Faber, Gerb & Soffen, LLP

[57] ABSTRACT

A method for mounting safety shields onto eyeglass temples and a kit for carrying out that method. A temple of an eyeglass frame is placed in a channel forming part of a side shield thereafter, a screw is inserted into an opening formed in the side shield and into a member affixed to the temple to create a fastened fit between the temple and the channel which attaches the side shield to the temple. The side shield is placed in its operative position before the screw is inserted into the opening and the fastened fit results from the insertion of the screw into the opening and member which holds the side shield in its operative position. The kit includes a side shield having a longitudinally extending channel into which a longitudinally extending eyeglass temple may be inserted. The channel has an open lateral end through which the temple may be inserted and a supporting lateral end against which the temple may be supported. The side shield further includes an opening extending transversely to both the longitudinal direction and the supporting lateral wall. A screw is adapted to be inserted into the opening and the member so as to force the temple against the supporting end of the channel to create a fastened fit between the side shield and the temple when the temple is located in the channel. Alternatively, a fastener is placed into the transverse open lateral end in the channel of the side shield, to receive a screw which is a adapted to be inserted into the fastener to create a fastened fit and prevent the temple from moving longitudinally within the channel of the side shield.

9 Claims, 4 Drawing Sheets

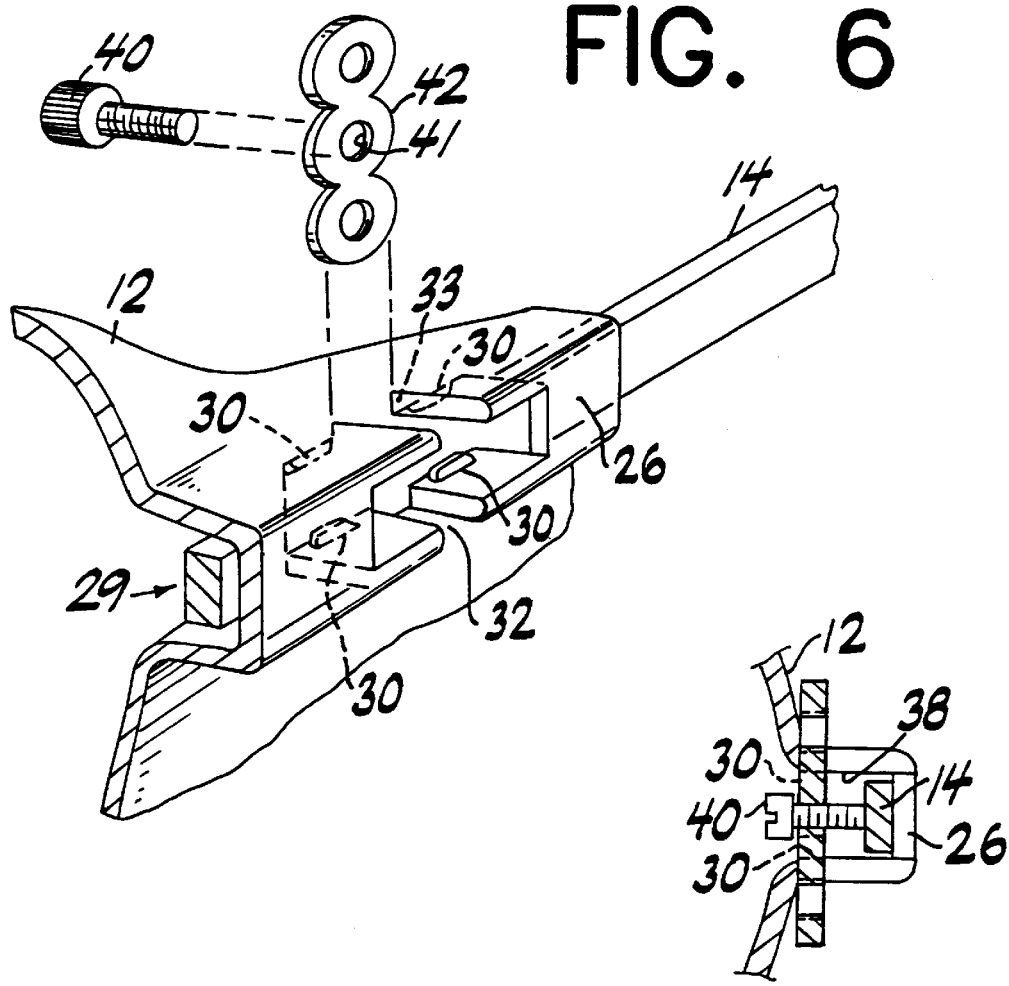
FIG. 6
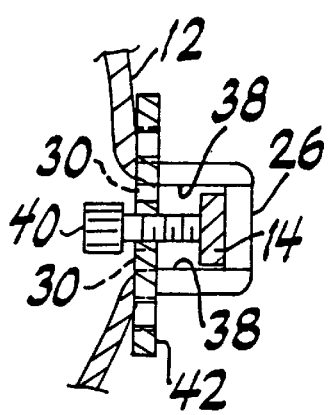
FIG. 7
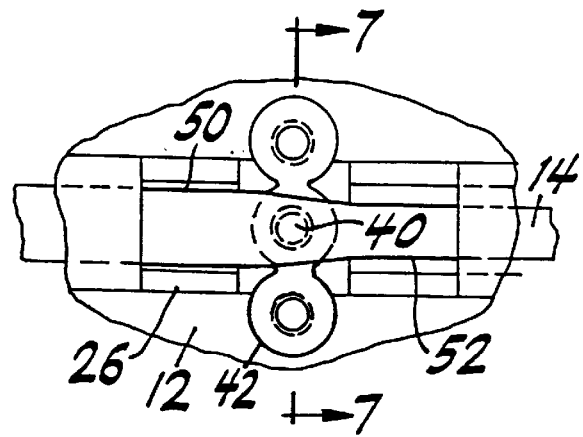
FIG. 8
FIG. 9

METHOD AND KIT FOR ATTACHING SIDE SHIELDS TO EYEGLASS TEMPLES

RELATED APPLICATION

This is a continuation of application Ser. No. 08/656,640, filed May 31, 1996, now U.S. Pat. No. 5,798,815.

BACKGROUND OF THE INVENTION

1. Field of the Invention

The present invention relates to a method for mounting safety shields onto eyeglass temples and a kit for carrying out that method.

2. Description of the Related Art

Conventional safety spectacles include side safety shields which are removably affixed. However, the case often arises where the employers do not want the employees removing the safety shields.

In the situations where the employer prefers that the shields be permanently affixed, the primary methods of attachment have been rivets, screws, lock-nuts or adhesives. In the prior art systems, the use of screws have required that holes be drilled in the temples of the glasses which has various drawbacks. Cutting a hole through the temple weakens the temples and often the temples break during drilling.

U.S. Pat. No. 3,505,679 discloses a pair of safety spectacles having removable side shields. Flanges of the side shield are snapped over the temple of the glasses. This is disadvantageous, as repeated placement and removal of the shields weakens the shield's flanges, and eventually the flanges will snap and the entire side shield must be replaced. Moreover, an employee can easily remove the shields, even if the employer requires the shields to be worn.

U.S. Pat. No. 3,721,490 discloses side shields which are permanently fastened to a pair of eyeglasses without the use of screws or adhesives. However, the attachment means are formed integrally with the side shields. Thus, not only is removal difficult, but once the shields are removed, they are not designed to be used again.

U.S. Pat. No. 3,165,754 teaches separate means for removably attaching the shields to temples of a pair of glasses. The attachment means comprise a support member having hooks for engaging a lens frame and a pair of sidewardly extending support arms which contact the top and bottom surfaces of the hinge between the temples and lens frame. The attachment means must be connected to the eyeglass frame and temples by a screw. Thus, simple installation is not possible.

SUMMARY OF THE INVENTION

The present invention makes it possible to secure side shields to the temples of a pair of glasses in such a manner that the shields cannot easily be removed and without the need to drill holes in the temple. In one preferred embodiment, the side shields are attached to the temples by a screw which fits into a bore formed in a member attached to the temple. With this embodiment, the side shields are "permanently" fastened to the temple in the sense that the screw must be removed in order to remove the side shields.

The method according to one embodiment of the present invention utilizes a temple of an eyeglass frame which has a member attached thereto, the member having a threaded bore formed therein. In accordance with the method, the side shield is attached to the temple by:

(a) placing the temple in a channel formed in part of the side shield; and thereafter (b) attaching the temple to the channel with a screw which is inserted into the threaded bore.

In the preferred embodiment, the side shield is initially placed in its operative position before the screw is inserted into the opening to fasten the side shield in the operative position.

The kit according to one embodiment of the present invention comprises:

(a) a side shield having a longitudinally extending channel into which a longitudinally extending eyeglass temple may be inserted, said channel having an open lateral end through which said temple may be inserted and a supporting lateral wall against which said temple may be supported and an opening through which a screw may be passed to extend into said channel; and (b) a member affixed to the temple and having a threaded bore formed therein for receiving a screw passed through said channel.

In this preferred embodiment, the side shield is initially placed in its operative position before the screw is inserted into a fastener that is placed into the transverse open end of the channel in the side shield to prevent the temple from freely moving within the channel of the side shield in the operative position.

The method according to a second embodiment of the invention utilizes a side shield having an elongated channel with a side wall, said method comprising the steps of:

(a) placing said temple in said channel adjacent said side wall; and thereafter (b) securing said temple against said side wall using a compressive locking arrangement.

The kit according to a second preferred embodiment of the present invention comprises:

(a) a side shield having a longitudinally extending channel into which a longitudinally extending eyeglass temple may be inserted, said channel having an open lateral end through which said temple may be inserted and a supporting lateral wall against which said temple may be supported and an opening through which a screw may be passed to extend into said channel; and (b) a lock washer capable of being placed into said channel with opposite ends of said lock washer extending through respective openings formed in said top and bottom walls, said lock washer having a threaded bore formed therein; and (c) a screw adapted to be screwed into said threaded bore of said lock washer so that, when a temple is located in said channel, and said lock washer is inserted into said openings formed in said top and bottom walls, an end of said screw will press said temple against said lateral side wall.

BRIEF DESCRIPTION OF THE DRAWINGS

For the purpose of illustrating the invention, there is shown in the drawings several forms which are presently preferred, it being understood, however, that the invention is not limited to the precise arrangements and instrumentalities shown.

FIG. 6 is a detailed partially exploded perspective view showing the manner in which the left side of the safety shield is secured to the left temple of the eyeglass frame in a second alternative of the present invention.

FIG. 7 is a cross sectional view taken along lines 7—7 of FIG. 8 showing the manner in which the left side of the safety shield is secured to the left temple of the eyeglass frame of FIG. 6.

FIG. 8 is a detailed partial perspective view showing the manner in which the left side of the safety shield is secured to the left temple of the eyeglass frame which prevents the side shield from being moved longitudinally along the eyeglass temple.

FIG. 9 is a cross sectional view taken along lines 7—7 of FIG. 8 showing the manner in which the left side of the safety shield is secured to the left temple of the eyeglass frame of FIG. 6 in a modification of the second alternative of the present invention.

DETAILED DESCRIPTION OF THE PREFERRED EMBODIMENTS

Figure 1:
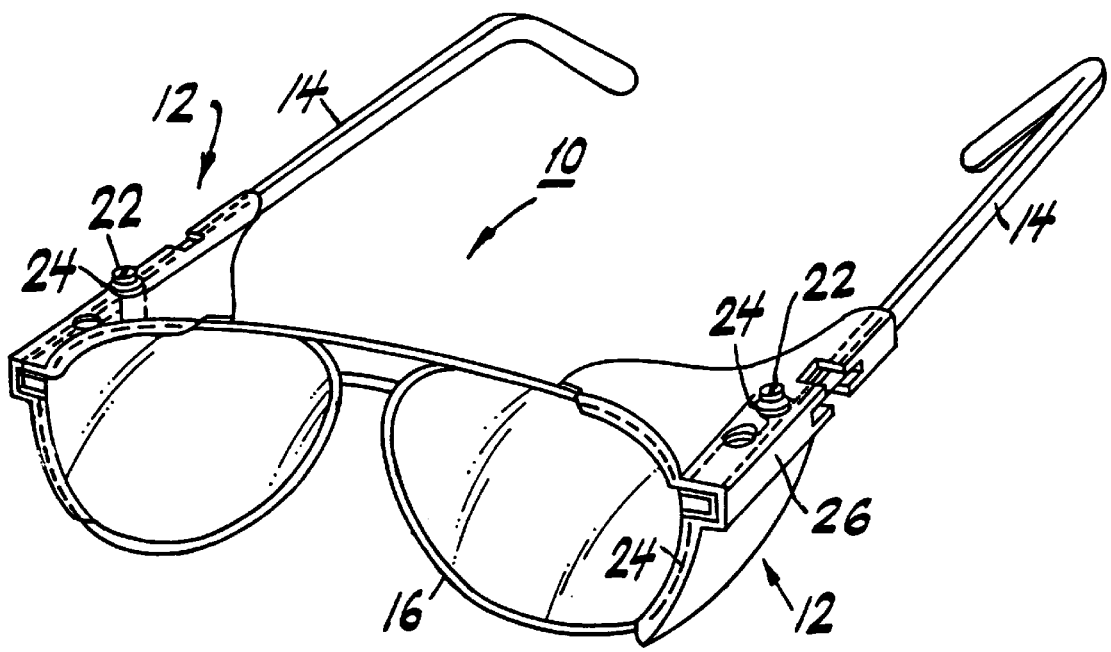
FIG. 1 is a perspective view of a pair of glasses having safety shields mounted thereto using a first embodiment of a kit according to the present invention.

Referring now to the drawings, wherein like numerals indicate like elements, there is shown in FIG. 1, a pair of eyeglasses 10 which have been made into safety glasses by the addition of side shields 12 coupled to the temples 14 of the eyeglass frames 16 in accordance with a preferred embodiment of the present invention.

Figure 2:
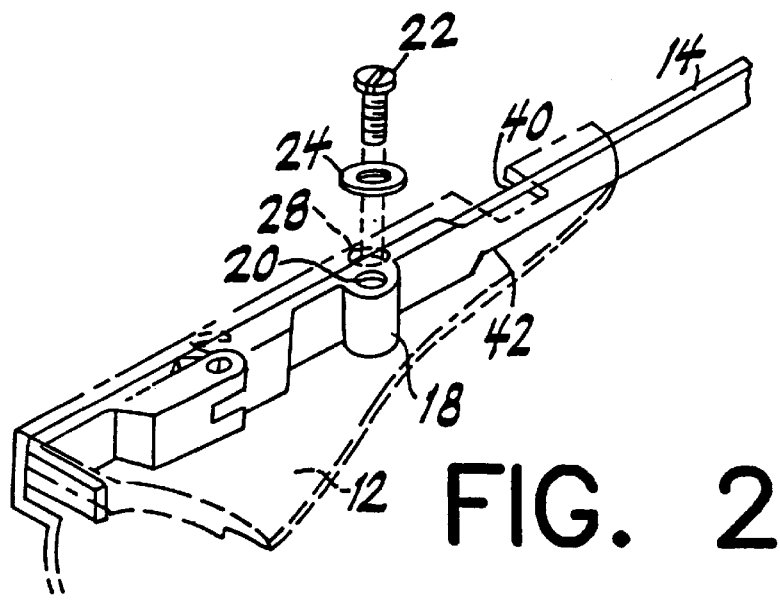
FIG. 2 is a detailed partially exploded perspective view showing the manner in which the right side of the safety shield is secured to the right temple of the eyeglass frame of FIG. 1.

The kit includes specially adapted temples 14 (one of which is shown in FIG. 2) which include a member 18, containing a threaded bore 20, which is either integrally formed on, or otherwise affixed to, the temple 14 of the eyeglass frame 16, a pair of side shields 12, a pair of connecting screws 22 for fastening the side shields 12 to the temples 14, and a pair of washers 24 (preferably made of plastic) for placement between the screws 22 and an opening 28 formed in the top of the side shields 12. The member 18 extends outwardly from the temples 14 so that the bore 20 does not weaken the temples. In the preferred embodiment, the side shields 12 wrap around the side and a portion of the top of the eyeglasses 10.

Figure 3:
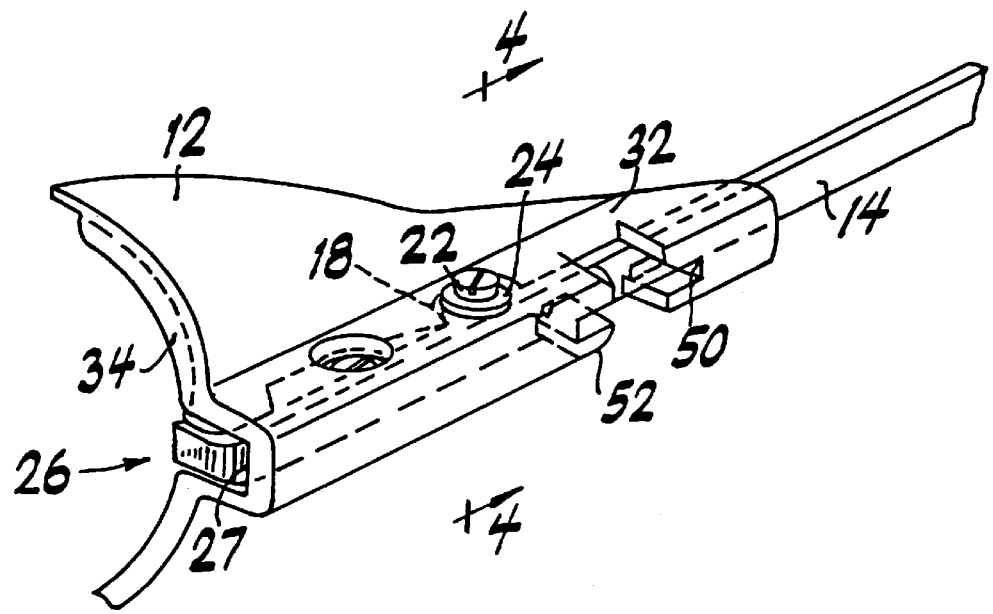
FIG. 3 is a detailed perspective view showing the manner in which the left side of the safety shield is secured to the left temple of the eyeglass frame of FIG. 1.

A longitudinally extending channel 26 is formed in each side shield 12 as best shown in FIG. 3. The channels 26 extend along a longitudinal axis and are adapted to closely receive a respective temple 14 of the eyeglass frame 16. Before the screw 22 is inserted into an opening 28 formed in the side shield 12, the temple 14 sits loosely within the channel adjacent a lateral side wall 27. See FIGS. 2 and 3. In the preferred embodiment, the channel 26 is formed integrally with the side shield 12. If desired, however, the channel 26 may be formed separately and connected to the side shield 12 by any appropriate means.

Four detents 30 (FIG. 6) are formed in the open lateral end 32 of the channel 26 to temporarily hold the temple 14 within the channel 26 before the side shield 12 is "permanently" attached to the temple 14 by insertion of the screw 22 into the opening 28 and the bore 20. Since the space between detents 30 is preferably smaller than the height of the temple 14 the temple is preferably inserted into the channel 26 in a position perpendicular to that illustrated in FIG. 3 and is then rotated into the position illustrated. Before the side shield 12 is "permanently" attached to the temple 14, it is placed in its operative position illustrated in FIG. 3. In this position, the front of eye shield 12 should be aligned with the front of the frame 16. Since the temple 14 fits loosely within the channel 26, the side shield 12 can easily be moved longitudinally along the temple 14 into the operative position. In the preferred embodiment, a lip 34 (FIG. 3) is formed on the front edge of the side shields 12 to partially cover the front of the eyeglass frame 16. Once the side shield 12 has been moved into the operative position, it is permanently fastened to the temple 14 by inserting the screw 22 into the opening 28 and the member 18.

Figure 2A:
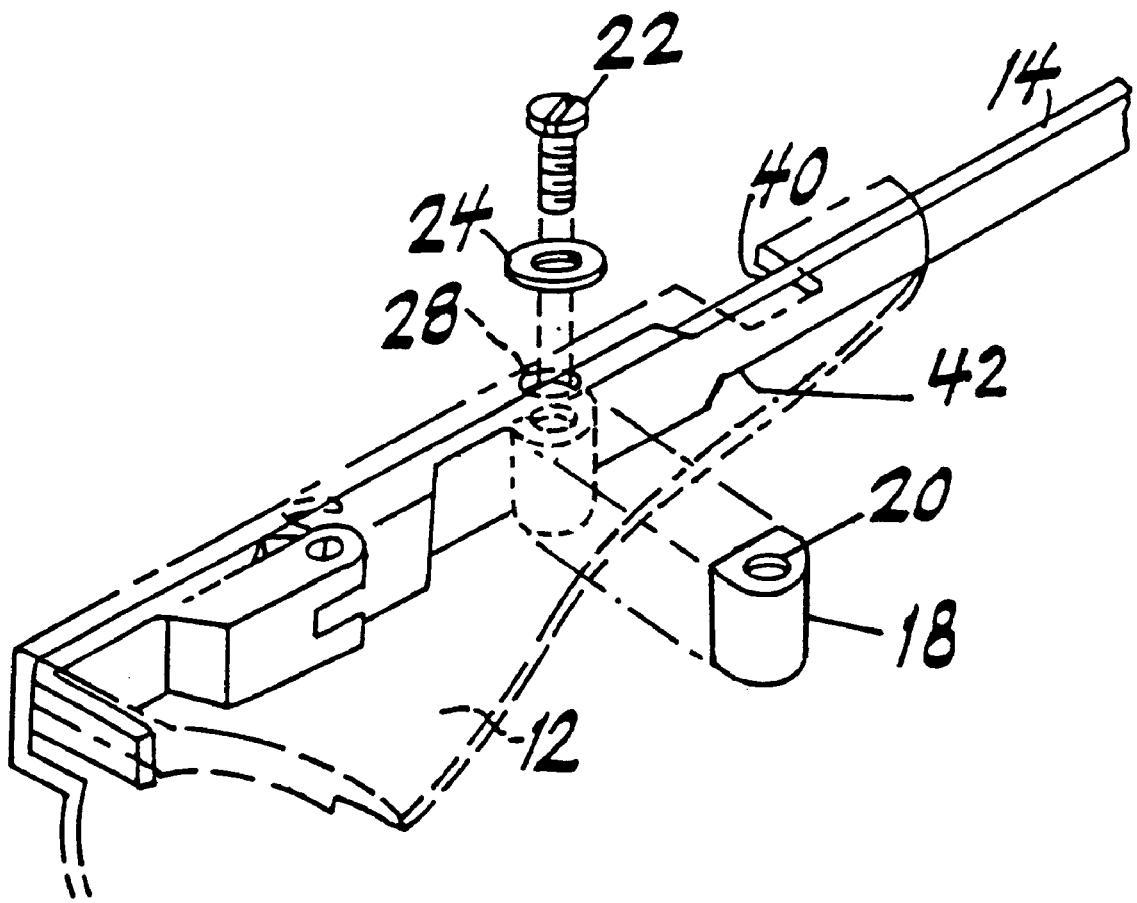
FIG. 2A is a detailed partially exploded perspective view showing a modification of the embodiment depicted in FIG. 2.

As best shown in FIG. 2, the member 18 having a threaded bore 20 formed therein is preferably integrally formed on the temple 14. Alternatively, it can be otherwise affixed to the temples 14. For example, the member 18 having a threaded bore 20 formed therein may be removable from the temple 14 as shown in FIG. 2A. By providing for a member 18 with a threaded bore 20 formed therein, it is not necessary to form any slots or holes in the temple 14 itself which would structurally weaken the temple 14. Additionally, there will be no unsightly hole in the temple 14 if the side shields 12 are removed since the member 18 is located on the inside of the temple 14 adjacent the wearer's head and is not seen when the glasses are worn.

Figure 4:
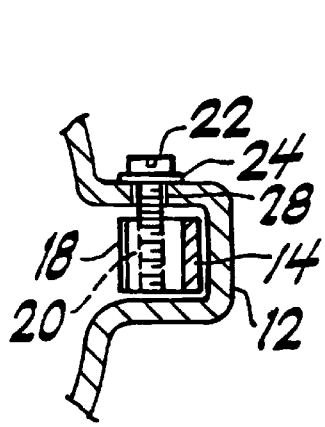
FIG. 4 is a cross sectional view taken along lines 4—4 of FIG. 3, wherein the screw has been inserted into its operative position.
Figure 5:
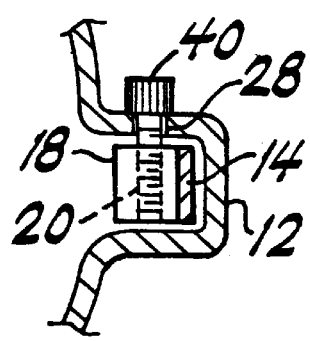
FIG. 5 is a cross sectional view taken along lines 4—4 of FIG. 3 showing a first modification of the first embodiment of the present invention.

The primary purpose of the opening 28 and the member 18 is to act as a receiving means for the screw 22 as the screw 22 is inserted into the threaded bore 20. The screw 22 operates to fasten the temple 14 and the side shield 12 elements together. Particularly, as the screw 22 is moved through the washer 24 and the opening 28 it is screwed into the threaded bore 20, and finally rests within the threaded bore 20 as shown in FIG. 4 between the temple 14 and the side edges 36, 38 (see FIG. 4) of the side shield 12 with the result that the temple 14 will become securely tightened into the channel 26. This captures the temple 14 within the channel 26 and makes it impossible to slide the channel 26 relative to the temple 14. The connection is not fully permanent since the screw 22 can be removed from the opening 28, at least with the aid of a tool such as a screwdriver.

To assist in the insertion process, the member 18 comprising the threaded bore 20 is located in a position directly beneath the opening 28 formed in the side shield 12.

Most people wearing eyeglass frames do not carry screwdrivers which are necessary to insert and remove the screw 22 from the opening 28 affixed to the temple 14. As an alternative to the first embodiment, it is often desirable to provide an easier means for inserting or removing a screw 22 from the opening 28 to fasten or take off the side shields 12.

In an alternative embodiment a thumbscrew 40 is used in lieu of a screw 22 to enable the user to more easily fasten or take off the side shields 12 from the eyeglass frames 16 with a thumb and index finger.

A second preferred embodiment of the present invention is shown in FIGS. 6, 7, 8 and 9 (the complete side shield 12 and its associated channel 26 are not illustrated). In this embodiment it is possible to fasten the side shields 12 to either a standard temple (or a specially adapted temple) of an eyeglass frame 44. The kit of this embodiment includes a pair of side shields 12, a pair of thumbscrews 40 for coupling the side shields 12 to the temples 14, and a pair of lock washers 42 which are adapted to fit into openings 32, 33 formed in the bottom and top walls of the channel 26 respectively.

In the preferred embodiment shown herein, the washer 42, the thumbscrew 40 and the openings 32, 33 cooperate to form a compressive locking arrangement which attaches the side shield 12 to the temple and which prevents longitudinal movement of the temple 44 relative to the side shield 12. See FIG. 6, 7 and 8.

Before the thumbscrew 40 is inserted into the lock washer 42, the temple 14 preferably sits loosely, but closely fitted, within the channel 26. Since the space between detents 30 is smaller than the height of the temple 14 (as best shown in FIG. 6), the temple is preferably inserted into the channel 26 in a position perpendicular to that illustrated in FIG. 6 and is then rotated into the position illustrated. Before the side shield 12 is "permanently" attached to the temple 14, it is placed in its operative position illustrated in FIG. 6. In this position, the front of the eye shield 12 should be aligned with the front of the frame 16. Since the temple 14 fits loosely within the channel 26, the side shield 12 can easily be moved longitudinally along the temple 14 into the operative position.

Once the side shield 12 has been moved into the operative position, it is permanently fastened to the temple 14 by inserting the washer 42 into the openings 32, 33 in the bottom and top walls and then inserting the thumbscrew 40 into the washer 42 as shown in FIGS. 6 and 7. The thumbscrew 40 is inserted perpendicular to the fastener 42 (FIG. 7).

The thumbscrew 40 and the opening 41 in the washer 42 are preferably threaded. The thumbscrew 40 operates to fasten the temple 14 and the side shield 12 elements together. Particularly, as the thumbscrew 40 is secured into the washer 42 it pushes the washer 42 against the edge of openings 32 and 33 and forces the temple 14 against the lateral side wall 27 of the channel 26. This captures the temple 14 within the channel 26 and makes it impossible to slide the channel 26 relative to the temple 14. Of course, the connection is not fully permanent since the thumbscrew 40 can be removed from the lock washer 42 with a thumb and index finger or other tool such as pliers or a wrench.

To assist in the insertion process, the lock washer 42 is preferably thin and rounded at the edges so as to allow it to fit between the temple 14 and the openings 32, 33 (See FIGS. 6, 7 and 8).

In a modification to the second embodiment, it is may be aesthetically desirable to utilize a screw 46 as a means for fastening the washer 42 to the side shields 12. In this modification shown in FIG. 9, a screw 46 enables one to fasten or take off the side shields 12 from the eyeglass frames 16 with a screwdriver or other tool.

The present invention may be embodied in other specific forms without departing from the spirit or essential attributes thereof and, accordingly, reference should be made to the appended claims, rather than to the foregoing specification, as indicating the scope of the invention.

What is claimed is:

1. A method of attaching a side shield to a temple of an eyeglass frame, said side shield having a side wall, said method comprising the steps of:

(a) placing said temple adjacent said side wall; and thereafter (b) securing said temple against said side wall using a screw and a washer which cooperate to press said temple against said side wall and retain said temple in a substantially fixed position relative to said side wall.

2. The method of claim 1, wherein said side shield includes an elongated channel into which said temple is placed, said elongated channel extending in a longitudinal direction and having an open end which is opposite said side wall and through which said temple is placed into said channel.

3. The method of claim 2, wherein said elongated channel has a generally u-shaped cross section.

4. The method of claim 2, wherein said securing step prevents said temple from being moved in said longitudinal direction of said temple.

5. The method of claim 1, wherein said screw and washer cooperate with other portions of said side shield to form a compressive locking arrangement.

6. The method of claim 1, wherein said washer has a threaded hole in operative engagement with said screw and wherein said washer lies in a plane which extends generally parallel to said sidewall and said screw extends generally perpendicular to said sidewall when said screw is screwed through said threaded hole.

7. The method of claim 6, wherein a pair of openings are formed in top and bottom walls of said channel and said washer is inserted into said pair of openings before said screw is screwed through said threaded hole in said washer.

8. The method of claim 7, wherein said screw is screwed through said threaded hole in such a manner that said washer presses against edges of said openings as said screw presses against said temple to form a compressive locking arrangement.

9. The method of claim 6, wherein said screw is a thumb screw.

* * * * *

(12) EX PARTE REEXAMINATION CERTIFICATE (5024th)
United States Patent
Hirschman et al.

(10) Number: US 5,940,161 C1
(45) Certificate Issued: *Nov. 23, 2004

(54) METHOD AND KIT FOR ATTACHING SIDE SHIELDS TO EYEGLASS TEMPLES

(75) Inventors: Richard Hirschman, Bohemia, NY (US); Wayne Jerman, Dallas, TX (US)

(73) Assignee: Hudson Optical Corporation, Henderson, NV (US)

Reexamination Request:
No. 90/006,636, May 13, 2003

Reexamination Certificate for:
Patent No.: 5,940,161
Issued: Aug. 17, 1999
Appl. No.: 09/092,436
Filed: Jun. 5, 1998

( * ) Notice: This patent is subject to a terminal disclaimer.

Related U.S. Application Data

(63) Continuation of application No. 08/656,640, filed on May 31, 1996, now Pat. No. 5,798,815.

(51) Int. Cl.[7] .............................. G02C 7/10; G02C 13/00
(52) U.S. Cl. ......................... 351/44; 351/121; 351/178; 2/13; 2/449
(58) Field of Search .......................... 351/44, 121, 111, 351/116, 158, 178, 47; 2/13, 448, 449, 450, 451

(56) References Cited

U.S. PATENT DOCUMENTS

| | | |
|---|---|---|
| 1,206,457 A | 11/1916 | Mills |
| 3,505,679 A | 4/1970 | Bennett .......................... 2/13 |
| 3,721,490 A | 3/1973 | Prince .......................... 351/47 |
| 4,123,132 A | 10/1978 | Hardy .......................... 339/246 |
| 4,507,809 A | 4/1985 | Stepan .......................... 2/424 |

FOREIGN PATENT DOCUMENTS

| | | |
|---|---|---|
| FR | 2 672 346 | 8/1992 |
| JP | 1-64618 | 4/1989 |
| JP | 2-117514 | 9/1990 |

*Primary Examiner*—Hung Dang

(57) ABSTRACT

A method for mounting safety shields onto eyeglass temples and a kit for carrying out that method. A temple of an eyeglass frame is placed in a channel forming part of a side shield thereafter, a screw is inserted into an opening formed in the side shield and into a member affixed to the temple to create a fastened fit between the temple and the channel which attaches the side shield to the temple. The side shield is placed in its operative position before the screw is inserted into the opening and the fastened fit results from the insertion of the screw into the opening and member which holds the side shield in its operative position. The kit includes a side shield having a longitudinally extending channel into which a longitudinally extending eyeglass temple may be inserted. The channel has an open lateral end through which the temple may be inserted and a supporting lateral end against which the temple may be supported. The side shield further includes an opening extending transversely to both the longitudinal direction and the supporting lateral wall. A screw is adapted to be inserted into the opening and the member so as to force the temple against the supporting end of the channel to create a fastened fit between the side shield and the temple when the temple is located in the channel. Alternatively, a fastener is placed into the transverse open lateral end in the channel of the side shield, to receive a screw which is a adapted to be inserted into the fastener to create a fastened fit and prevent the temple from moving longitudinally within the channel of the side shield.

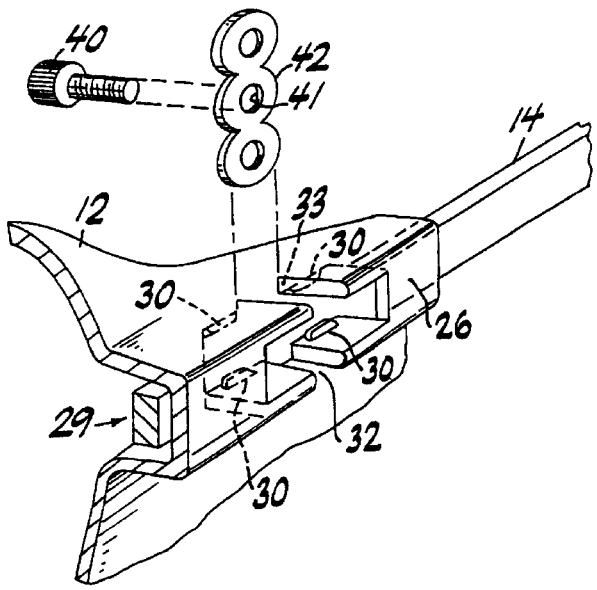

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–9 is confirmed.

\* \* \* \* \*